United States Patent
Bennett et al.

(10) Patent No.: US 10,921,245 B2
(45) Date of Patent: Feb. 16, 2021

(54) METHOD AND SYSTEMS FOR REMOTE EMISSION DETECTION AND RATE DETERMINATION

(71) Applicant: Ball Aerospace & Technologies Corp., Boulder, CO (US)

(72) Inventors: Mats D. Bennett, Spring Valley, OH (US); Jason Monnin, Fairborn, OH (US); Jarett Levi Bartholomew, Longmont, CO (US); Cynthia Wallace, Louisville, CO (US); Lyle Ruppert, Longmont, CO (US); Reuben Rohrschneider, Boulder, CO (US); Bevan D. Staple, Longmont, CO (US); William Tandy, Superior, CO (US)

(73) Assignee: Ball Aerospace & Technologies Corp., Boulder, CO (US)

( * ) Notice: Subject to any disclaimer, the term of this patent is extended or adjusted under 35 U.S.C. 154(b) by 60 days.

(21) Appl. No.: 16/235,827

(22) Filed: Dec. 28, 2018

(65) Prior Publication Data

US 2019/0376890 A1 Dec. 12, 2019

Related U.S. Application Data

(60) Provisional application No. 62/682,513, filed on Jun. 8, 2018, provisional application No. 62/682,516, filed on Jun. 8, 2018.

(51) Int. Cl.
  *G01N 21/39* (2006.01)
  *G01M 3/38* (2006.01)
  (Continued)

(52) U.S. Cl.
  CPC ............. *G01N 21/39* (2013.01); *G01M 3/22* (2013.01); *G01M 3/38* (2013.01); *G01S 17/89* (2013.01); *G01N 2021/394* (2013.01)

(58) Field of Classification Search
  CPC ............ G01M 3/22; G01M 3/38; G01S 17/89
  See application file for complete search history.

(56) References Cited

U.S. PATENT DOCUMENTS

| 3,856,402 A | 12/1974 | Low et al. |
| 3,925,666 A | 12/1975 | Allan et al. |

(Continued)

FOREIGN PATENT DOCUMENTS

| CA | 1305767 | 7/1992 |
| CA | 2509540 | 7/2004 |

(Continued)

OTHER PUBLICATIONS

Aerius Photonics website, "Aerius NIR/SWIR Illuminators" product sheet, available at www.aeriusphotonics.com/datasheets.html, 2 pages (2009).

(Continued)

*Primary Examiner* — Edward Park
(74) *Attorney, Agent, or Firm* — Sheridan Ross P.C.

(57) ABSTRACT

Methods and systems for remotely detecting gases and emissions of gases are provided. Data is collected from a scene using a sensor system. The data is initially optionally processed as 1D data to remove noise, and is then assigned a confidence value by processing the 1D data using a neural network. The confidence value is related to a likelihood that an emission has been detected at a particular location. The processed 1D data, including the confidence value, is gridded into 2D space. The 2D data is then processed using a neural network to assign a 2D confidence value. The 2D data can be fused with RGB data to produce a map of emission source locations. The data identifying emissions can also be processed using a neural network to determine and output emission rate data.

20 Claims, 7 Drawing Sheets

(51) Int. Cl.
  *G01S 17/89* (2020.01)
  *G01M 3/22* (2006.01)

(56) References Cited

U.S. PATENT DOCUMENTS

| | | |
|---|---|---|
| 4,022,532 A | 5/1977 | Montagnino |
| 4,059,356 A | 11/1977 | Kebabian |
| 4,201,468 A | 5/1980 | Margolis et al. |
| 4,286,877 A | 9/1981 | Clarke |
| 4,425,503 A | 1/1984 | Watkins et al. |
| 4,450,356 A | 5/1984 | Murray et al. |
| 4,489,239 A | 12/1984 | Grant et al. |
| 4,567,366 A | 1/1986 | Shinohara |
| 4,730,320 A | 3/1988 | Hidaka et al. |
| 4,772,789 A | 9/1988 | Maram et al. |
| 4,870,275 A | 9/1989 | Ozdemir |
| 5,001,346 A | 3/1991 | Barkhoudarian |
| 5,015,099 A | 5/1991 | Nagai et al. |
| 5,029,023 A | 7/1991 | Bearden et al. |
| 5,087,125 A | 2/1992 | Narutaki |
| 5,091,778 A | 2/1992 | Keeler |
| 5,149,959 A | 9/1992 | Collins et al. |
| 5,157,257 A | 10/1992 | Geiger |
| 5,179,422 A | 1/1993 | Peterson |
| 5,192,978 A | 3/1993 | Keeler |
| 5,239,860 A | 8/1993 | Harris et al. |
| 5,250,810 A | 10/1993 | Geiger |
| 5,262,645 A | 11/1993 | Lambert et al. |
| 5,298,751 A | 3/1994 | Fee et al. |
| 5,317,376 A | 5/1994 | Amzajerdi et al. |
| 5,345,304 A | 9/1994 | Allen |
| 5,357,371 A | 10/1994 | Minott |
| 5,485,009 A | 1/1996 | Meyzonnetie et al. |
| 5,528,354 A | 6/1996 | Uwira |
| 5,544,186 A | 8/1996 | Sauer et al. |
| 5,552,893 A | 9/1996 | Akasu |
| 5,682,225 A | 10/1997 | DuBois et al. |
| 5,682,229 A | 10/1997 | Wangler |
| 5,767,519 A | 6/1998 | Gelbwachs |
| 5,784,023 A | 6/1998 | Bluege |
| 5,790,188 A | 8/1998 | Sun |
| 5,793,034 A | 8/1998 | Wesolowicz et al. |
| 5,815,250 A | 9/1998 | Thomson et al. |
| 5,847,816 A | 12/1998 | Zediker et al. |
| 5,870,180 A | 2/1999 | Wangler |
| 5,870,181 A | 2/1999 | Andressen |
| 5,914,776 A | 6/1999 | Streicher |
| 5,917,596 A | 6/1999 | Jenkins et al. |
| 5,923,466 A | 7/1999 | Krause et al. |
| 6,034,770 A | 3/2000 | Kim et al. |
| 6,173,066 B1 | 1/2001 | Peurach et al. |
| 6,323,941 B1 | 11/2001 | Evans et al. |
| 6,327,037 B1 | 12/2001 | Chou et al. |
| 6,384,903 B1 | 5/2002 | Fuller |
| 6,411,871 B1 | 6/2002 | Lin |
| 6,414,746 B1 | 7/2002 | Stettner et al. |
| 6,434,211 B1 | 8/2002 | Lloyd et al. |
| 6,448,572 B1 | 9/2002 | Tennant et al. |
| 6,509,566 B1 | 1/2003 | Wamsley et al. |
| 6,542,831 B1 | 4/2003 | Moosmuller et al. |
| 6,597,505 B1 | 7/2003 | Chaney et al. |
| 6,608,669 B2 | 8/2003 | Holton et al. |
| 6,646,725 B1 | 11/2003 | Eichinger et al. |
| 6,657,733 B1 | 12/2003 | Drake |
| 6,664,529 B2 | 12/2003 | Pack et al. |
| 6,665,063 B2 | 12/2003 | Jamieson et al. |
| 6,690,472 B2 | 2/2004 | Kulp et al. |
| 6,697,155 B2 | 2/2004 | Dobbs et al. |
| 6,747,258 B2 | 6/2004 | Benz et al. |
| 6,804,607 B1 | 10/2004 | Wood |
| 6,822,742 B1 | 11/2004 | Kalayeh et al. |
| 6,943,868 B2 | 9/2005 | Haig |
| 6,972,887 B2 | 12/2005 | Wickham et al. |
| 7,006,203 B1 | 2/2006 | Book et al. |
| 7,027,924 B2 | 4/2006 | Spoonhower et al. |
| 7,067,812 B2 | 6/2006 | Gelbwachs |
| 7,075,653 B1 | 7/2006 | Rutherford |
| 7,095,488 B2 | 8/2006 | Jamieson et al. |
| 7,113,886 B2 | 9/2006 | West |
| 7,142,981 B2 | 11/2006 | Hablani |
| 7,221,436 B1 | 5/2007 | Mendenhall et al. |
| 7,224,466 B2 | 5/2007 | Ray |
| 7,224,707 B2 | 5/2007 | Gendron |
| 7,236,235 B2 | 6/2007 | Dimsdale |
| 7,240,879 B1 | 7/2007 | Cepollina et al. |
| 7,260,507 B2 | 8/2007 | Kalayeh |
| 7,277,641 B1 | 10/2007 | Gleckman |
| 7,298,869 B1 | 11/2007 | Abernathy |
| 7,312,452 B2 | 12/2007 | Klingenberg et al. |
| 7,333,184 B2 | 2/2008 | Kalayeh |
| 7,342,228 B1 | 3/2008 | O'Connell et al. |
| 7,345,743 B1 | 3/2008 | Hartman et al. |
| 7,349,094 B2 | 3/2008 | Harris et al. |
| 7,359,057 B2 | 4/2008 | Schwiesow |
| 7,361,922 B2 | 4/2008 | Kameyama et al. |
| 7,385,705 B1 | 6/2008 | Hoctor et al. |
| 7,397,568 B2 | 7/2008 | Bryce et al. |
| 7,406,220 B1 | 7/2008 | Christensen et al. |
| 7,411,196 B2 | 8/2008 | Kalayeh |
| 7,414,726 B1 | 8/2008 | Bambeck |
| 7,414,727 B2 | 8/2008 | Willing et al. |
| 7,436,494 B1 | 10/2008 | Kennedy et al. |
| 7,453,552 B1 | 11/2008 | Miesak et al. |
| 7,456,970 B1 | 11/2008 | Lopez et al. |
| 7,474,685 B2 | 1/2009 | Kalayeh |
| 7,486,399 B1 | 2/2009 | Reichardt et al. |
| 7,508,520 B1 | 3/2009 | Lines et al. |
| 7,532,311 B2 | 5/2009 | Henderson et al. |
| 7,580,132 B2 | 8/2009 | Baillon et al. |
| 7,705,988 B2 | 4/2010 | Richman |
| 7,755,041 B2 | 7/2010 | Killinger et al. |
| 7,961,301 B2 | 6/2011 | Earhart et al. |
| 7,995,917 B2 | 8/2011 | Mendenhall et al. |
| 8,010,300 B1 | 8/2011 | Stearns et al. |
| 8,013,303 B2 | 9/2011 | Ershov et al. |
| 8,077,294 B1 | 12/2011 | Grund et al. |
| 8,121,798 B2 | 2/2012 | Lippert et al. |
| 8,229,679 B1 | 7/2012 | Matthews |
| 8,269,971 B1 | 9/2012 | Marsh et al. |
| 8,294,899 B2 | 10/2012 | Wong |
| 8,306,273 B1 | 11/2012 | Grayseth et al. |
| 8,345,250 B1 | 1/2013 | Janosky et al. |
| 8,379,208 B1 | 2/2013 | Simmons et al. |
| 8,395,771 B2 | 3/2013 | Izawa et al. |
| 8,559,721 B1 | 10/2013 | Bartholomew et al. |
| 8,730,461 B2 | 5/2014 | Andresi |
| 8,736,818 B2 | 5/2014 | Weimer et al. |
| 8,781,755 B2 | 7/2014 | Wong |
| 8,823,938 B2 | 9/2014 | Beck et al. |
| 9,030,663 B2 | 5/2015 | Braun et al. |
| 9,037,413 B1 | 5/2015 | Rodgers et al. |
| 9,097,646 B1 | 8/2015 | Campbell et al. |
| 9,442,012 B2 | 9/2016 | Mann et al. |
| 9,534,893 B2 | 1/2017 | Tulet et al. |
| 2002/0117340 A1 | 8/2002 | Stettner |
| 2002/0118352 A1 | 8/2002 | Ohzu et al. |
| 2003/0030001 A1 | 2/2003 | Cooper et al. |
| 2003/0063884 A1 | 4/2003 | Smith et al. |
| 2004/0021852 A1 | 2/2004 | DeFlumere |
| 2004/0119838 A1 | 6/2004 | Griffis et al. |
| 2004/0130702 A1 | 7/2004 | Jupp et al. |
| 2004/0213463 A1 | 10/2004 | Morrison |
| 2004/0263852 A1 | 12/2004 | Degtiarev et al. |
| 2005/0018743 A1 | 1/2005 | Volodin et al. |
| 2005/0052636 A1 | 3/2005 | Lee et al. |
| 2005/0060092 A1 | 3/2005 | Hablani |
| 2005/0099634 A1 | 5/2005 | Dubois et al. |
| 2005/0160822 A1 | 7/2005 | Langdon |
| 2006/0088946 A1 | 4/2006 | Willson et al. |
| 2006/0114447 A1 | 6/2006 | Harris et al. |
| 2006/0132752 A1 | 6/2006 | Kane |
| 2006/0136172 A1 | 6/2006 | O'Kane et al. |
| 2006/0197936 A1 | 9/2006 | Liebman et al. |
| 2006/0203248 A1 | 9/2006 | Reichardt et al. |

(56) References Cited

U.S. PATENT DOCUMENTS

| | | |
|---|---|---|
| 2007/0018104 A1 | 1/2007 | Parvin et al. |
| 2007/0073486 A1 | 3/2007 | Tillotson et al. |
| 2007/0090861 A1 | 4/2007 | Andersen et al. |
| 2007/0110364 A1 | 5/2007 | Rice et al. |
| 2007/0115541 A1 | 5/2007 | Rogers et al. |
| 2007/0122001 A1 | 5/2007 | Wang et al. |
| 2007/0171407 A1 | 7/2007 | Cole et al. |
| 2007/0263676 A1 | 11/2007 | Beukema et al. |
| 2008/0023587 A1 | 1/2008 | Head et al. |
| 2008/0136626 A1 | 6/2008 | Hudson et al. |
| 2008/0212328 A1 | 9/2008 | Minano et al. |
| 2008/0259340 A1 | 10/2008 | Prasad et al. |
| 2008/0273560 A1 | 11/2008 | Stelmakh |
| 2008/0290259 A1 | 11/2008 | Mathewson et al. |
| 2008/0316498 A1 | 12/2008 | Drake et al. |
| 2009/0001262 A1* | 1/2009 | Visser .................. G06K 9/6242 250/282 |
| 2009/0002680 A1 | 1/2009 | Ruff et al. |
| 2009/0046289 A1 | 2/2009 | Caldwell et al. |
| 2009/0059201 A1 | 3/2009 | Willner et al. |
| 2009/0080695 A1 | 3/2009 | Yang |
| 2009/0110267 A1 | 4/2009 | Zakhor et al. |
| 2009/0115994 A1 | 5/2009 | Stettner et al. |
| 2009/0142066 A1 | 6/2009 | Leclair et al. |
| 2009/0237640 A1 | 9/2009 | Krikorian et al. |
| 2009/0273770 A1 | 11/2009 | Bauhahn et al. |
| 2009/0310118 A1 | 12/2009 | Halldorsson |
| 2010/0110204 A1 | 5/2010 | Campbell et al. |
| 2010/0165323 A1 | 6/2010 | Fiess et al. |
| 2010/0182587 A1 | 7/2010 | Fluckiger |
| 2010/0315631 A1 | 12/2010 | Zhou et al. |
| 2011/0038507 A1 | 2/2011 | Hager |
| 2011/0074931 A1 | 3/2011 | Bilbrey et al. |
| 2011/0222063 A1 | 9/2011 | Izawa et al. |
| 2012/0154813 A1 | 6/2012 | Li et al. |
| 2012/0163791 A1 | 6/2012 | Juri et al. |
| 2013/0242131 A1 | 9/2013 | Timm |
| 2013/0335599 A1 | 12/2013 | Zhang |
| 2014/0005958 A1* | 1/2014 | Baliga ..................... G06N 3/02 702/51 |
| 2014/0158870 A1 | 6/2014 | DeAntonio et al. |
| 2014/0300798 A1 | 10/2014 | Sapir |
| 2014/0362880 A1 | 12/2014 | Chuang et al. |
| 2015/0022809 A1 | 1/2015 | Marchant et al. |
| 2015/0323449 A1 | 11/2015 | Jones et al. |
| 2016/0188936 A1 | 6/2016 | Nunnink et al. |
| 2016/0214715 A1 | 7/2016 | Meffert |
| 2016/0238854 A1 | 8/2016 | Kammans |
| 2016/0274025 A1 | 9/2016 | Skibo et al. |
| 2016/0300336 A1 | 10/2016 | Pacifici |
| 2017/0089829 A1 | 3/2017 | Bartholomew |
| 2017/0358068 A1* | 12/2017 | Strebel .................... G01S 17/89 |
| 2018/0315440 A1* | 11/2018 | Inaba ........................ G06F 40/40 |
| 2019/0115267 A1* | 4/2019 | Kabouzi .................. H01L 22/20 |
| 2019/0187020 A1* | 6/2019 | Green ..................... G08B 25/08 |
| 2019/0376890 A1* | 12/2019 | Bennett ............. G01N 21/3151 |

FOREIGN PATENT DOCUMENTS

| | | |
|---|---|---|
| CA | 2630301 | 6/2007 |
| CA | 2386268 C | 2/2012 |
| CA | 2458123 C | 5/2012 |
| CN | 201575308 | 9/2010 |
| CN | 102261909 | 11/2011 |
| CN | 102829938 | 12/2012 |
| CN | 104457708 | 3/2013 |
| CN | 103364781 | 10/2013 |
| CN | 103528680 | 3/2015 |
| CN | 105300912 | 2/2016 |
| CN | 105300925 | 2/2016 |
| CN | 105761214 | 7/2016 |
| CN | 106199939 | 12/2016 |
| CN | 106236006 | 12/2016 |
| EP | 190280 | 8/1986 |
| EP | 0489546 | 6/1992 |
| EP | 0578129 | 1/1994 |
| GB | 2127537 | 9/1986 |
| GB | 2300325 | 10/1996 |
| GB | 2306828 | 5/1997 |
| GB | 2311852 | 12/1999 |
| GB | 2364840 | 2/2002 |
| JP | H06-301113 | 10/1994 |
| JP | 2004-007413 | 1/2004 |
| JP | 04987360 | 7/2012 |
| JP | 2016-080629 | 5/2016 |
| RU | 2091759 | 9/1997 |
| WO | WO 01/18563 | 3/2001 |
| WO | WO 02/04982 | 1/2002 |
| WO | WO 02/065155 | 8/2002 |
| WO | WO 03/079582 | 9/2003 |
| WO | WO 2006/130734 | 12/2006 |
| WO | WO 2007/081628 | 7/2007 |
| WO | WO 2009/115122 | 9/2009 |
| WO | WO 2009/133414 | 11/2009 |
| WO | WO 2016/029305 | 3/2016 |
| WO | WO 2016/033452 | 3/2016 |
| WO | WO 2016/041079 | 3/2016 |
| WO | WO 2016/076724 | 5/2016 |
| WO | WO 2016/161284 | 10/2016 |

OTHER PUBLICATIONS

"BMW Develops Laser Light for the Car," BMW Corporate Communications Press Release, BMW Group, Sep. 1, 2011, 3 pages.
"Flash LIDAR Technology Shows Promise for Vegetation Canopy Science Measurements," NASA Earth Science and Technology Office, 2009, 2 pages.
"The Infrared & Electro-Optical Systems Handbook: Passive Electro-Optical Systems," Infrared Information Analysis Center, 1993, Stephen B. Campana, Editor, 362 pages.
Abad et al. "Integrating synthetic objects into real scenes," Computers & Graphics, Feb. 2003, vol. 27, No. 1, pp. 5-17.
Abdalati et al., Report of the Ad-Hoc Science Definition Team for the Ice Cloud and Land Elevation Satellite-II (ICESAT-II), 2008, 69 pages.
Allen et al., "Full-Scale Testing and Platform Stabilization of a Scanning Lidar System for Planetary Landing", Space Exploration Technologies (Wolfgang Fink, ed.), Proceedings of SPIE, vol. 6960, pp. 696004-1-696004-10 (2008).
Allen et al., "Rendezvous Lidar Sensor System for Terminal Rendezvous, Capture, and Berthing to the International Space Station", Sensors and Systems for Space Applications II, SPIE vol. 6958, 8 pages(2008).
Aull et al., "Geiger-Mode Avalanche Photodiodes for Three-Dimensional Imaging", Lincoln Laboratory Journal, vol. 13, No. 2 (2002).
Bakalski et al., "Real Time Processing Enables Fast 3D Imaging at Single Photon Level", Laser Radar Technology and Applications XIII, (Monte D. Turner, Gary W. Kamerman, ed.), Proceedings of the SPIE, vol. 6950, pp. 69500K-1-69500K-9 (2008).
Baker et al., "Advanced Infrared Detectors for Multimode Active and Passive Imaging Applications" Infrared Technologies and Applications XXXIV (Bjorn F. Andresen, Gabor F. Fulop, and Paul R. Norton, ed.), Proceedings of the SPIE, vol. 6940, pp. 69402L-1-69402L-11 (2008).
Boldt et al., "A Handheld Texel Camera for Acquiring Near-Instantaneous 3D Images," Conference Record of the Forty-First Asilomar Conference on Signals, Systems & Computers, Nov. 4, 2007, pp. 953-957.
Brady et al., "ALHAT System Architecture and Operational Concept", Aerospace Conference, 2007 IEEE, Big Sky, MT, IEEEAC Paper # 1570, Version 4, pp. 1-13 (2007).
Brake "Detection and Measurement of Fugitive Emissions Using Airborne Differential Absorption Lidar (DIAL)," ITT Space Systems Division, Apr. 2006, 11 pages.
Bruneau et al. "Simultaneous measurements of particle backscattering and extinction coefficients and wind velocity by lidar with a

(56) References Cited

OTHER PUBLICATIONS

Mach-Zehnder interferometer: principle of operation and performance assessment," Applied Optics, Feb. 2003, vol. 42, No. 6, pp. 1101-1114.
Bruneau, "Mach-Zehnder Interferometer as a Spectral Analyzer for Molecular Doppler Wind Lidar", Applied Optics, vol. 40, No. 3, pp. 391-399 (2001).
Chen et al., "RANSAC-Based Darces: A New Approach to Fast Automatic Registration of Partially Overlapping Range Images", IEEE Transactions on Pattern Analysis and Machine Intelligence, vol. 21, No. 11, 6 pages (Nov. 1999).
Cho et al., "Real-Time 3D Ladar Imaging", 35th Applied Imagery and Pattern Recognition Workshop, pp. 5 (2006).
Connes et al., "Astronomical Fourier Spectrometer", Applied Optics, vol. 14, No. 9, pp. 2067-2084 (1975).
Coyle et al., "The High Output Maximum Efficiency Resonator (HOMER) Developed for Long Life, Space-Based Altimetry," IEEE Aerospace Conference, 2006, 7 pages.
Craig et al., "Processing 3D Flash LADAR Point-Clouds in Real-Time for Flight Applications", Sensors and Systems for Space Applications (Richard T. Howard and Robert D. Richards, ed.), Proceedings of SPIE, vol. 6555, pp. 65550D-1-65550D-9 (2007).
De Lafontaine et al., "LAPS: The Development of a Scanning Lidar System with GNC for Autonomous Hazard Avoidance and Precision Landing"; Spaceborne Sensors (Robert D. Habbit, Jr. and Peter Tchoryk, Jr., ed.), Proceedings of SPIE, vol. 5418, pp. 81-93 (2004).
Degnan, "Photon-Counting Multikilohertz Microlaser Altimeters for Airborne and Spaceborne Topographic Measurements", Journal of Geodynamics, vol. 34, pp. 503-549 (2002).
De Jong et al. "IR panoramic alerting sensor concepts and applications," Infrared Technology and Applications XXIX, Proceedings of SPIE vol. 5074, Apr. 2003, pp. 658-668.
Dissly et al., "Flash LIDAR Systems for Planetary Exploration", American Astronomical Society, DPS Meeting, Presentation # 40, Ithaca, NY, Bulletin of the American Astronomical Society, vol. 41, pp. 560 (2008).
Durrani et al., "Spectral Analysis and Cross-Correlation Techniques for Photon Counting Measurements on Fluid Flows", Applied Optics, vol. 14, No. 3, pp. 778-794 (1975).
Fay et al., "Fusion of Multi-Sensor Passive and Active 3D Imagery", Enhanced and Synthetic Vision 2001 (Jacques G. Verly, ed.), Proceedings of SPIE, vol. 4363, pp. 219-230 (2001).
Fenton et al., "Simulation Tests of a Lidar-based Spacecraft Pose Determination Algorithm", Sensors and Systems for Space Applications, SPIE vol. 6555, 11 pages (2007).
Fenton, "A LADAR-Based Pose Estimation Algorithm for Determining Relative Motion of a Spacecraft for Autonomous Rendezvous and Dock", Master of Science thesis, Utah State University, 90 pages (2008).
Forkuo et al. "Automatic Fusion of Photogrammetric Imagery and Laser Scanner Point Clouds," Department of Land Surveying & Geo-Informatics, The Hong Kong Polytechnic University, 2005, 6 pages.
Gaudin-Delrieu et al. "The High Resolution Optical Instruments for the Pleiades HR Earth Observation Satellites," International Conference on Space Optics, 2008, Oct. 14-17 Toulouse, France, 7 pages.
Gault, et al., "ERWIN: An E-Region Wind Interferometer", Applied Optics, vol. 35, No. 16, pp. 2913-2922 (1996).
Gentry et al., "The Tropospheric Wind Lidar Technology Experiment (TWiLiTE): An Airborne Direct Detection Doppler Lidar Instrument Development Program", available at www.esto.nasa.gov/conferences/estc2006/papers/b8p2.pdf.
Gillula, "Data Fusion From Multiple Sensors: Real-Time Mapping on an Unmanned Ground Vehicle", 2005 SURF Final Report, California Institute of Technology, 13 pgs (2005).
Goff et al. "Focal Plane AIT Sequence: Evolution From HRG-Spot 5 to Pleiades HR," Proceedings of the 6th International Conference on Space Optics, ESTEC, Jun. 27-30 2006, Noordwijk, The Netherlands, 6 pages.
Grund et al. "Simultaneous Profiling of Aerosol Optical Properties, Gas Chemistry, and Winds with Optical Autocovariance Lidar", Paper 1 of 2 presented at the 24th International Laser Radar Conference, Jun. 23-27, 2008, 5 pages.
Grund et al. "Enabling Characteristics of Optical Autocovariance Lidar for Global Wind and Aerosol Profiling", AGU, American Geophysical Union, Fall Meeting, San Francisco, CA (Dec. 16, 2008).
Grund et al., "Optical Autocovariance Wind Lidar (OAWL) for Efficient Space-Based Direct-Detection High-Resolution Aerosol Backscatter Winds", Paper 2 of 2 presented at the 24th International Laser Radar Conference, Jun. 23-27, 2008, 5 pages.
Grund et al., "Optical Autocovariance Wind Lidar and Performance from LEO", 14th Coherent Laser Radar Conference, Snowmass, CO (Jul. 7, 2007).
Grund et al., "Supporting NOAA and NASA High-Performance Space-Based DWL Measurement Objectives with a Minimum Cost, Mass, Power, and Risk Approach Employing Optical Autocovariance Wind Lidar (OAWL)", Space Winds Lidar Working Group, Monterrey, CA (Feb. 6, 2008).
Grund et al., "Optical Autocovariance Wind Lidar (OAWL) for Efficient Space-Based Direct-Detection High-Resolution Aerosol Backscatter Winds", International Laser Radar Conference, Boulder, CO (Jun. 24, 2008), 1 page.
Grund et al., Poster Entitled "Optical Autocovariance Wind Lidar (OAWL) for Efficient Space-Based Direct-Detection High-Resolution Aerosol Backscatter Winds", presented at the Coherent Laser Radar Conference, Jul. 2007, presented at the Working Group on Space-based Lidar Winds, Feb. 2008, and presented at the International Laser Radar Conference, Boulder, CO, Jun. 23-27, 2008, 1 page.
Grund et al., Presentation Entitled "Optical Autocovariance Wind Lidar and Performance from LEO", presented at the Coherent Laser Radar Conference, Jul. 11, 2007, 30 pages.
Grund et al., Presentation Entitled "Simultaneous Profiling of Aerosol Optical Properties, Gas Chemistry, and Winds with Optical Autocovariance Lidar", 24th ILRC Conference (Jun. 23, 2008).
Grund, "An Alternative Direct Detection Approach to Doppler Winds that is Independent of Aerosol Mixing Ratio and Transmitter Frequency Jitter", Space Winds Lidar Working Group, Miami, FL (Feb. 8, 2007).
Grund, "Lidar Wind Profiling from Geostationary Orbit Using Imaging Optical Autocovariance Interferometry", Space Winds Lidar Working Group, Snowmass, CO (Jul. 17, 2007).
Grund, Christian J., Power Point Presentation Entitled "Optical Autocovariance: Alternative Direct Detection Approach to Doppler Winds that is Independent of Aerosol Mixing Ratio and Transmitter Frequency Jitter", presented at the Working Group Conference on Space-Based Lidar Winds, Feb. 6-9, 2007, 12 pages.
Habbit et al., "Utilization of Flash LADAR for Cooperative and Uncooperative Rendezvous and Capture", Space Systems Technology and Operations (Peter Tchoryk, Jr. and James Shoemaker, ed.), Proceedings of SPIE, vol. 5088, pp. 146-157 (2003).
Hancock et al. "Shallow-Depth 3D Interaction: Design and Evaluation of One-, Two- and Three-Touch Techniques," CHI 2007 Proceedings, Apr. 28-May 3, 2007, San Jose, CA, USA, pp. 1147-1156.
Hyde et al., "Mapping Forest Structure for Wildlife Habitat Analysis Using Multi-Sensor (LiDAR, SAR/InSAR, ETM+, Quickbird) Synergy", Remote Sensing of Environment, vol. 102, pp. 63-73 (2006).
Jacquinot, "The Luminosity of Spectrometers with Prisms, Gratings, or Fabry-Perot Etalons", Journal of the Optical Society of America, vol. 44, No. 10, pp. 761-765 (1954).
Jasiobedzki et al., "Autonomous Satellite Rendezvous and Docking Using LIDAR and Model Based Vision", Spaceborne Sensors II, SPIE vol. 5798, 12 pages (2005).
Kasten, et al., "Fabrication and Characterization of Individually Addressable Vertical-Cavity Surface-Emitting Laser Arrays and Integrated VCSEL/PIN Detector Arrays", Proceedings of SPIE, vol. 6484, 64840C, 2007.
Kumar et al., "Determination of the Instrument Function of a Grating Spectrometer by Using White-Light Interferometry", Applied Optics, vol. 36, No. 19, pp. 4535-4539 (1997).

(56) References Cited

OTHER PUBLICATIONS

Lamoreux et al., "Relative Navigation Sensor for Autonomous Rendezvous and Docking", Laser Radar Technology and Applications VIII (Gary W. Kamerman, ed.), Proceedings of the SPIE, vol. 5086, pp. 317-328 (2003).
Ledebuhr et al., "Micro-Satellite Ground Test Vehicle for Proximity and Docking Operations Development," Aerospace Conference, Mar. 10-17, 2001, IEEE Proceedings, Jan. 1, 2001, vol. 5, pp. 2493-2504.
Lefsky et al., "Estimates of Forest Canopy Height and Aboveground Biomass Using ICESat", Geophysical Research Letters, vol. 32, L2202, 4 pages (2005).
Lenz et al. "Flight Testing of an Advanced Airborne Natural Gas Leak Detection system," ITT Industries Space Systems, LLC, Oct. 2005, 84 pages.
Lieber et al., "Development of a Validated End-to-End Model for Space-Based Lidar Systems", Lidar Remote Sensing for Environmental Monitoring VIII (Singh, Upendra N. ed.), Proceedings of the SPIE, vol. 6681, 66810F (2007).
Lieber et al., "Integrated System Modeling for Evaluating the Coronagraph Approach to Plant Detection", High-Contrast Imaging for Exo-Planet Detection (Schultz, Alfred B. ed.), Proceedings of the SPIE, vol. 4860 (2002). (Abstract only).
Lieber, Mike et al., "System Verification of the JMEX Mission Residual Motion Requirements with Integrated Modeling", UV/Optical/IR Space Telescopes: Innovative Technologies and Concepts II (MacEwen, Howard A. ed.), Proceedings of the SPIE, vol. 5899, 589901, pp. 1-12 (2005).
Marino et al., "Jigsaw: A Foliage-Penetrating 3D Imaging Laser Radar System"; Lincoln Laboratory Journal, vol .15, No. 1, pp. 23-36 (2005).
Mayo, Jr., "Photon Counting Processor for Laser Velocimetry", Applied Optics, vol. 16, No. 5, pp. 1157-1162 (1977).
Mitchell et al. "Remote Methane Sensor Using Tuneable Diode Laser Spectroscopy (TDLS) Via A 1W Raman Source," Proceedings of SPIE, Oct. 2009, vol. 7503, 750350, 4 pages.
Morton, "Photon Counting", Applied Optics, vol. 7, No. 1, pp. 1-10 (1968).
Oberle et al., "Toward High Resolution, Ladar-Quality 3-D World Models Using Ladar-Stereo Data Integration and Fusion," Army Research Laboratory, ARL-TR-3407, 37 pgs (2005).
Pack et al., "A Co-Boresighted Synchronized Ladar/EO Imager for Creating 3D Images of Dynamic Scenes", Laser Radar Technology and Applications, X (Gary W. Kamerman, ed.), Proceedings of SPIE, vol. 5791, pp. 42-50 (2005).
Pierrottet et al., "Characterization of 3-D Imaging Lidar for Hazard Avoidance and Autonomous Landing on the Moon"; Laser Radar Technology and Applications XII (Monte D. Turner and Gary W. Kamerman, ed.), Proceedings of SPIE, vol. 6550, pp. 655008-1-655008-9 (2007).
Pranyies et al. "SiC Focal Plane Assembly for the PLEIADES HR Satellite," Sensosrs, Systems, and Next-Generation Satellites VIIIL, Proceedings of SPIE vol. 5570, Sep. 13, 2004, pp. 568-576.
Rabinovich et al., "45 Mbps Cat's Eye Modulating Retro-Reflector Link Over 7 Km", Free-Space Laser Communications VI, Proceedings of the SPIE, vol. 6304, pp. 63040Q (2006). (Abstract only).
Richardson et al., "Design and Performance Considerations of Cat's Eye Retroreflectors for Use in Open-Path Fourier-Transform-Infrared Spectrometry", Applied Optics, vol. 41, No. 30, pp. 6332-6340 (2002).
Ring et al., "Field-Compensated Michelson Spectrometers", Applied Optics, vol. 11, No. 3, pp. 507-516 (1972).
Riris et al., "The Lunar Orbiter Laser Altimeter (LOLA) on NASA's Lunar Reconnaissance Orbirot (LRO) Mission", Sensors and Systems for Space Applications (Richard T. Howard and Robert D. Richards, ed.), Proceedings of SPIE, vol. 6555, pp. 655501-1-655501-8 (2007).
Roberts, Jr. et al., "Aperture Sharing Between Low-Background Infrared Sensors and Ladar Sensors", Aerospace Applications Conference, Proceedings of the IEEE, vol. 4, pp. 495-508 (1996).

Ronnholm et al. "Integration of Laser Scanning and Photogrammetry," Proceedings of the ISPRS Workshop on Laser Scanning 2007 and SilviLaser 2007, Sep. 2007, vol. 36, Part 3, pp. 355-362.
Ruel et al., "Field Testing of a 3D Automatic Target Recognition and Pose Estimation Algorithm", Automatic Target Recognition XIV, SPIE vol. 5426, 10 pages (2004).
Ruel et al., "Real-Time 3D Vision Solution for On-Orbit Autonomous Rendezvous & Docking", Spaceborne Sensors III, SPIE 6220, 11 pages (2006).
Scherello "State of the art methane leak detection CHARM® and GasCam®," Open Grid Europe, Oct. 2011, 33 pages.
Shepherd et al., "WAMDII: Wide-Angle Michelson Doppler Imaging Interferometer for Spacelab", Applied Optics, vol. 24, No. 11, pp. 1571-1584 (1985).
Shepherd et al., "WINDII—The Wind Imaging Interferometer for the Upper Atmosphere Research Satellite", Geophys. Res. vol. 98, No. D6, pp. 10,725-10,750 (1993).
Shugart et al., "Determination of Stand Properties in Boreal and Temperate Forests Using High-Resolution Imagery," Forest Science, 2000, vol. 46, No. 4, pp. 478-486.
Smith et al., "Diffractive Optics for Moon Topography Mapping"; Micro (MEMS) and Nanotechnologies for Space Applications (Thomas George and Zhong-Yang Cheng, ed.), Proceedings of SPIE, vol. 6223, pp. 622304-1-622304-10 (2006).
Stentz et al., "Real-Time, Multi-Perspective Perception for Unmanned Ground Vehicles", Proceedings of the Association for Unmanned Vehicle Systems International, 15 pgs (2003).
Stettner et al., "Three Dimensional Flash Ladar Focal Planes and Time Dependent Imaging," International Symposium on spectral Sensing Research, May 31, 2006, retrieved at www.advancedscientific-concepts.com/technology/documents/ThreeDimensionalFlashLabdarFocalPlanes-ISSSRPaper.pdf, 5 pages.
Tan et al., "Design and Performance of a Multiwavelength Airborne Polarimetric Lidar for Vegetation Remote Sensing"; Journal of Applied Optics, vol. 43, No. 11, pp. 2360-2368 (2004).
Trenkle et al., "3D Sensor Algorithms for Spacecraft Pose Determination", Spaceborne Sensors III (Richard T Howard and Robert D. Richards, ed.), Proceedings of SPIE, vol. 6220, pp. 62200D-1-62200D-14 (2006).
Vallerga et al., "Noiseless, High Frame Rate (>KHz), Photon Counting Arrays for Use in the Optical to the Extreme UV", University of California, Berkeley—Sciences Laboratory and University of Geneva, Switzerland, available at www.ssl.berkeley.edu/~mcphate/AO/ao_medipix.html (2004-present).
Vasile et al., "Pose-Independent Automatic Target Detection and Recognition Using 3D Laser Radar Imagery", Lincoln Laboratory Journal, vol. 15, No. 1, 18 pages (2005).
Wang et al., "Optimized Reflective Wide-Angle Michelson Phase-Stepping Interferometer", Applied Optics, vol. 39, No. 28, pp. 5147-5160, (2000).
Weimer et al., "Seeing the Forest and the Trees: An electronically steerable flash LiDAR improves vegetation studies," Earth Imaging Journal, 2009, pp. 33-34.
Weinberg et al., "Flash Lidar Systems for Hazard Detection, Surface Navigation and Autonomous Rendezvous and Docking", 2007 LEAG Workshop on Enabling Exploration, 2 pgs (2007).
Weishampel et al., "Semivariograms from a forest transect gap model compared with remotely sensed data," Journal of Vegetation Science, 1992, vol. 3, Iss. 4, pp. 521-523 (Abstract only).
Wikipedia, "RANSAC", available at http://en.wikipedia.org/wiki/RANSAC, 5 pages (2009).
Xun et al., "Expanding range of pulsed range sensors with active projection from spatial light modulators", Spaceborne Sensors III, Proc. of SPIE vol. 6220, 62200I, 2006, 9 pages.
Yoon et al., "High Frequency Attitude Motion of ICESat", Advances in Astronautical Sciences (David A. Vollado, Michael J. Gabor and Prasun N. Desai ed.), vol. 120: Spaceflight Mechanics, Part 1, pp. 117-131 (2005).
Zhu et al. "Probing methane in air with a midinfrared frequency comb source," Applied Optics, Aug. 2017, vol. 56, No. 22, pp. 6311-6316.

(56) References Cited

OTHER PUBLICATIONS

Bartholomew et al. "Wide Area Methane Emissions Mapping with Airborne IPDA LiDAR," Proceedings of SPIE, Aug. 30, 2017, vol. 10406, 1040607, 14 pages.
Wang et al. "A41F-0105: Two-stream Convolutional Neural Network for Methane Emissions Quantification," AGU Fall Meeting 2017, Dec. 14, 2017, 1 page.
International Search Report and Written Opinion for International (PCT) Patent Application No. PCT/US2019/029413, dated Sep. 6, 2019 13 pages.

* cited by examiner

METHOD AND SYSTEMS FOR REMOTE EMISSION DETECTION AND RATE DETERMINATION

CROSS-REFERENCE TO RELATED APPLICATIONS

This application claims the benefit of U.S. Provisional Patent Application Ser. No. 62/682,513, filed Jun. 8, 2018, and the benefit of U.S. Provisional Patent Application Ser. No. 62/682,516, filed Jun. 8, 2018, the entire disclosures of which are hereby incorporated herein by reference.

FIELD

Systems and methods for the remote detection, source localization, and quantification of gas plumes are provided.

BACKGROUND

In 2015, methane accounted for 655 million kilograms of the 7.1 billion kilograms of greenhouse gases released into the atmosphere of the United States alone. The energy sector was responsible for just under half of the methane released, amounting to about 279 million kg of lost product with a value of hundreds of millions of dollars. As a result, detecting leaks from the 2.6 million miles of natural gas pipelines snaking across America is properly both a business and an environmental priority. Air surveillance has reduced serious pipeline leaks by 39 percent since 2009, but there have still been 250 serious incidents in the past 8 years. These include a San Bruno, Calif., pipeline blast that killed eight people in 2010 and the Aliso Canyon leak in 2016, which released about 97 million kilograms of methane, essentially doubling the Greater Los Angeles area's usual volume of methane emissions from all sources for a three month period. Until now, efforts to detect what the industry calls "fugitive emissions" have been constrained by the instrument sensitivity and response times. While airborne surveillance is possible using conventional techniques, it has traditionally required low-flying, slow-moving, expensive-to-run helicopters.

In addition to the limitations in techniques for detecting leaks or other emissions, the ability to determine leak rates has been an evolving field. One classical approach is to estimate leak rates from visual observations of plume shapes. This technique has proven prone to large errors, and can be slow and inefficient. Alternatively, leak rates have been estimated using complex, phenomenological models (such as the Gaussian plume model), which requires information regarding local wind speeds and other parameters. However, while these approaches can be faster, they are also prone to errors.

SUMMARY

Systems and methods for detecting emissions of a gas of interest are provided. Moreover, using systems and methods disclosed herein, emission sources can be located and quantified. Embodiments of the present disclosure enable the detection and rate of leaks to be determined remotely and in real-time or near real-time. The systems and methods can be implemented in connection with a platform, including but not limited to an airplane, helicopter, balloon, or unmanned aerial vehicle (UAV).

A system in accordance with embodiments of the present disclosure can include a sensor system or other instrument capable of remotely detecting the presence of a gas of interest in the atmosphere. Suitable sensor systems include, but are not limited to, a light detection and ranging (LIDAR) system, a differential absorption lidar (DIAL), a tunable laser system, a thermal camera, a diffractive spectrometer, a Fabry Perot spectrometer, wavelength filters, a Fourier transform spectrometer, and a frequency comb spectrometer. In at least some embodiments, a sensor system incorporating a DIAL instrument is described with some particularity. However, it should be appreciated that embodiments of the present disclosure are not necessarily limited thereto.

As can be appreciated by one of skill in the art after consideration of the present disclosure, a DIAL instrument gas detection system uses two lasers of slightly different infrared wavelengths to map the ground and measure an atmospheric gas of interest, such as, but not limited to, methane. For example, a DIAL system uses two lasers of closely-spaced wavelengths. Methane strongly absorbs one of the wavelengths (e.g. at about 1645.55 nm, the "on-resonance beam") and is virtually transparent to the other (e.g. at about 1645.4 nm, the "off-resonance beam"). The laser light bounces off the ground and scatters back to the receiver, and the system calculates the intensity differences between the returns to measure the amount of methane in the beams' paths. Return pulses may be sharply reflected by solid ground, distorted by foliage, or, in the case of the on-resonance pulse, completely absent because they have been fully absorbed by high concentrations of methane. These can provide more than two wavelengths and can map gas absorption features in greater detail. Another system in accordance with embodiments of the present disclosure include a passive spectrometer that relies on solar photon absorption in the gas of interest. An understanding of the atmosphere, view angles, and other factors allows the instrument to derive absorption values along the light path. A third approach is thermal infrared detection where cameras and microbolometers operating in the 1-14 µm wavelength range can detect emissions and absorptions from the environment, including the gases of interest.

The sensor system can additionally include a navigation unit or system, such as a global positioning system (GPS) receiver or an inertial measurement or navigation unit (INU). The data obtained by the instruments can be spatially correlated, and can be geo-referenced using data from the GPS receiver and/or INU. In addition, the sensor system can include a context camera that operates to obtain a 2D image, such as a red, green, blue (RGB) visual image of a scene. The visual image data obtained by the context camera can be combined or correlated with the data obtained by the instrument to enhance the identification and location of emission plumes.

Systems in accordance with embodiments of the present disclosure further include a computer, controller, or other elements that operate to execute instructions for implementing a neural network. The instructions may be encoded by an application stored in data storage or memory included in the system. An output from the system may be provided as a human perceivable map of the location and rate of detected emissions (e.g. leaks).

The present disclosure provides a novel method for converting signals from systems such as these into high-confidence gas plume detections using a combination of one-dimensional (1D) and two-dimensional (2D) spatially and temporally correlated and uncorrelated noise reduction techniques and signal processing. For example, Long Short-Term Memory (LSTM)/with artificial neural network including but not limited to a convolutional neural network (CNN), or deep neural networks (DNN)). In addition, embodiments of the present disclosure can be implemented for real-time processing (e.g., using GPU hardware).

Embodiments of the present disclosure provide unique and novel systems and methods that use deep learning to extract emission rates directly, without requiring wind measurements, from various factors, including plume shape, 3D range surface roughness, and contextual imagery. In at least some embodiments, the emission rates of detected plumes are determined in real-time or near real-time.

Additional features and advantages of embodiments of the disclosed systems and methods will become more readily apparent from the following description, particularly when taken together with the accompanying drawings.

DETAILED DESCRIPTION

Figure 1:
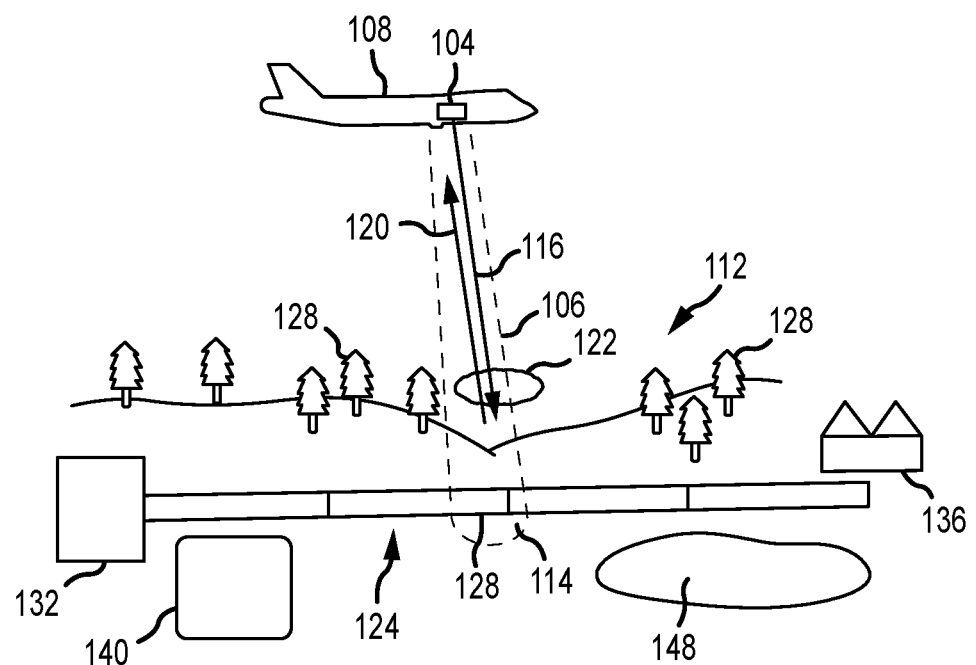
FIG. 1 depicts an arrangement for sensing gas emissions in accordance with embodiments of the present disclosure.

FIG. 1 depicts an emission detection scenario using a sensor or detection system 104 in accordance with embodiments of the present disclosure. The scenario can include monitoring of known, intentional, or fugitive emissions. In particular embodiments, the sensor system 104 is a remote sensor system incorporating an optical detection mechanism capable of remotely detecting the presence of a gas of interest, such as but not limited to methane. A sensor system 104 in accordance with embodiments of the present disclosure can include, but is not limited to, a light detection and ranging (lidar) system, a differential absorption lidar (DIAL), a tunable laser system, a thermal camera, a diffractive spectrometer, a Fabry Perot spectrometer, wavelength filters, a Fourier transform spectrometer, and a frequency comb spectrometer.

In the depicted scenario, the remote sensing system 104 is mounted to a platform 108. In this example, the platform 108 is an airplane, however, other mobile or even stationary platforms 108 may be associated with the sensor system 104. Examples of other mobile platforms 108 include satellites, helicopters, unmanned aerial vehicles, autonomous rovers, balloons, cars, all-terrain vehicles, ships, or other mobile platforms. Examples of stationary platforms 108 include radio towers, power transmission towers, observation towers, telephone poles, or other stationary supports. In general, the platform 108 is used to place the sensor system 104 in a location from which a survey area, target region, or scene 112 is observed. When the sensor system 104 is in a desired position with respect to the scene 112, it is operated to obtain measured data from the scene 112. For instance, wherein the sensor system 104 incorporates a LIDAR, DIAL instrument, laser spectrometer, or frequency comb spectrometer, the sensor system 104 is operated to output illumination light 116 and to pass that light through a target volume 106 to illuminate a target area or areas 114 within the scene 112. Reflected light 120 is returned from the target area 114 within the scene 112, and is detected by the sensor system 104. In the case of a system 104 incorporating a type of LIDAR, information regarding the time of flight of the light is used to obtain range information between the sensor system 104 and the target area 114 within the scene 112. Information regarding the amplitude of the reflected light 120 is used to obtain information regarding the concentration of a gas of interest 122 within the target volume 106. In a passive system, information comprising measured values taken at one or more wavelengths can be collected from the target area 114. The scene 112 can include a manmade facility 124 or a natural feature under inspection or monitoring. Examples of a facility, structure, or area 124 that can be inspected or monitored using a sensor system 104 as disclosed herein include pipelines 128, wellheads 132, factories 136, agricultural zones 140, or the like. Moreover, it should be appreciated that a sensor system 104 can include active and passive instruments that are operated in conjunction with one another to cooperatively obtain measured values from within a scene 112.

As can be appreciated by one of skill in the art after consideration of the present disclosure, different target areas 114 comprising different elements or features within a scene 112 will result in different obtained or measured values. For instance, in an active system that illuminates a target area 114, different elements or features will reflect the illumination light 116 differently. For example, a terrain feature comprising a forested hillside 128 may reflect the illumination light 116 less efficiently than a lake or pond 148. As a further example, an area within the scene 112 covered by snow will typically reflect the illumination light 116 more efficiently than bare ground. Accordingly, in the case of a sensor system 104 incorporating a DIAL, corrections can be made for the different reflectivities of surfaces within a target area 114. In particular, the strength of a return 120 resulting from illumination light 116 of a first wavelength that is strongly absorbed by a gas of interest 122 is compared to the strength of a return 120 resulting from illumination light 116 of a second wavelength that is not strongly absorbed by the gas of interest. A difference in the strength of the returns for a given background or portion of a scene indicates that the gas of interest 122 is present in a target volume 106. Moreover, the amount of such a difference is indicative of a concentration of the gas of interest 122 within the target volume 106.

As can also be appreciated by one of skill in the art after consideration of the present disclosure, the detection of emissions, and information regarding the location at which an emission of a gas of interest 122 is detected, is important to efficiently addressing a potential leak or other unauthorized or undesired emission. Accordingly, a sensor system 104 in accordance with at least some embodiments of the present disclosure can include a two-dimensional context camera, in addition to an active laser or lidar system and/or a passive system. Still other embodiments of the present disclosure can additionally or alternatively include a three-dimensional imaging type sensor that is used in connection with detecting the reflected light 120. In accordance with further embodiments of the present disclosure, the sensor system 104 can include an infrared camera.

Figure 2:
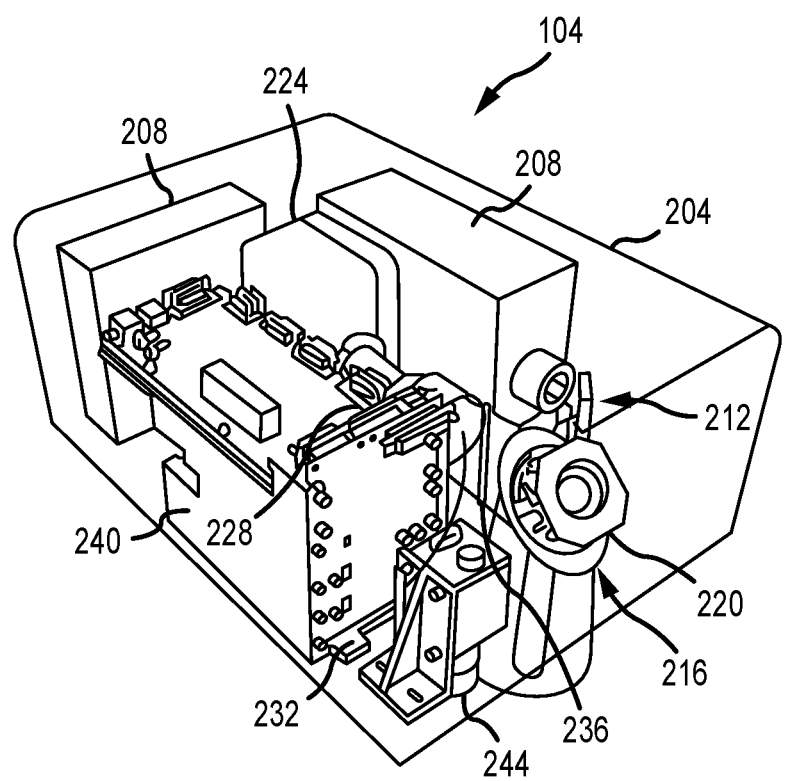
FIG. 2 depicts a sensor system in accordance with embodiments of the present disclosure.

FIG. 2 depicts a sensor system 104 accordance with at least some embodiments of the present disclosure. In this example, the sensor system 104 incorporates a DIAL instrument. However, other instruments for detecting emissions of a gas or gasses of interest can be used as an alternative or in addition to a DIAL instrument. For instance, the sensor system 104 can include a lidar, a passive spectrometer, a thermal infrared detection system, or a combination of different instruments or sensors. More particularly, examples include, in addition to a DIAL instrument, a lidar system, a tunable laser system, a thermal camera, a diffractive spectrometer, a Fabry Perot spectrometer, wavelength filters, a Fourier transform spectrometer, and a frequency comb spectrometer. In general, the sensor system 104 features a shared enclosure or frame 204 that carries or encloses various components of the system 104. These components can include one or more light source assemblies 208, a beam coupling assembly 212, and transmit optics 216. The transmit optics 216 can include a wide-angle steering mirror 220. Alternatively or in addition, the transmit optics 216 can be mounted to a gimbal, to allow the field of view to be pointed at a target area 114. In accordance with still other embodiments of the present disclosure, the entire sensor system 104, or selected portions of the sensor system 104, can be mounted to a gimbal. The components of the system 104 can additionally include a detector 224, such as a single pixel detector or a multiple pixel array detector. The detector 224 can be associated with an imaging lens or a receive telescope 228, which can include an infrared lens 232. In accordance with at least some embodiments of the present invention, the transmit optics 216 and the receive telescope 228 can share the steering mirror 220. In such embodiments, a mirror or a beam splitter/combiner 236 can be provided to direct light between the steering mirror 220, the transmit optics 216, and the receive optics 228. The enclosure 204 can additionally house electronics 240, such as processors, driver circuits, memory, communications devices, and the like, and a context camera 244, as discussed in greater detail elsewhere herein.

Figure 3:
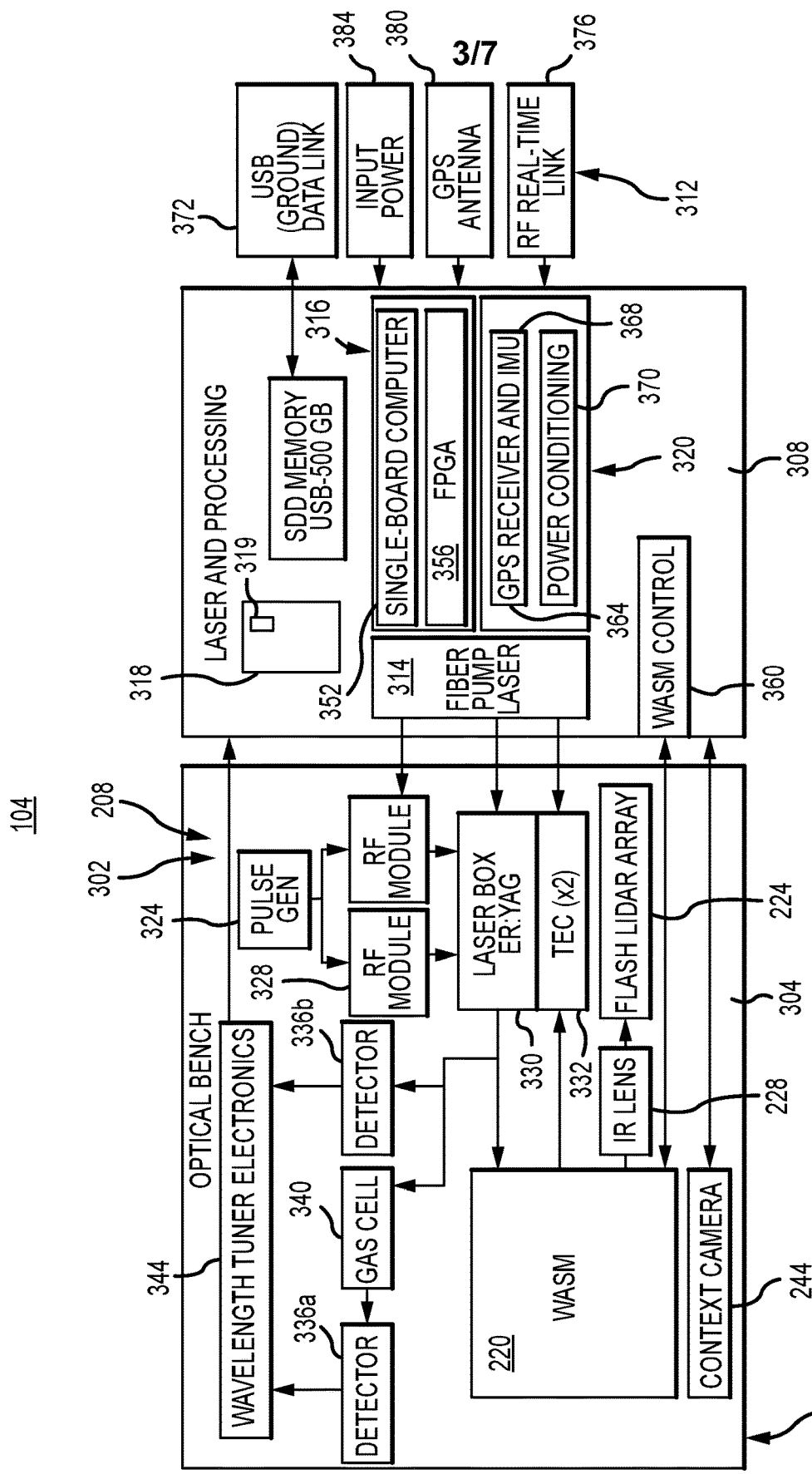
FIG. 3 is a block diagram depicting components of a sensor system in accordance with embodiments of the present disclosure.

FIG. 3 is a block diagram depicting components of an example sensor system 104 incorporating a DIAL instrument in accordance with embodiments of the present disclosure. In this functional depiction, the components of the sensor system 104 can generally be divided into those that are part of an optical bench 304, part of a light source and processing section 308, or associated with input/output functions 312.

The optical bench 304 generally includes components that direct illumination light 116 from the light source assemblies 208 towards the target area 114, and sensors, such as a detector or flash lidar array sensor 224, for implementing a 3D or lidar system 302 sensor. Pulse generation 324 and radio frequency module 328 components that interact with one or more laser boxes or cavities 330 and thermoelectric controllers 332 can be included to control the output wavelength of laser pulses as transmitted light 116. The optical bench 304 can further include a laser monitoring assembly 306 comprising components for monitoring the output of the light from a cavity 330. Parameters of the light that are monitored can include the intensity and wavelength. The components of the laser monitoring assembly 306 can include detectors 336a and 336b, at least one of which is associated with a gas cell 340, and wavelength tuner electronics 344 that can operate to provide a feedback signal to the light source and processing section 308. Still other components that can be included as part of the optical bench 304 are the steering mirror 220, which can be implemented as a wide-angle steering mirror, the context camera 244, the detector 224, and an imaging lens or receive telescope 228 that directs light received at the steering mirror 220 as reflected light 120 to the detector 224.

The light source and processing section 308 generally includes one or more light sources or lasers 314, signal processing and control components 316 provided as part of the electronics 240, and positioning, control, and power components 320. The light sources 314 output light that is delivered to the optical bench 304 to be transmitted to a target area 114 as illumination light 116. The positioning, control, and power components 316 section can more include a computer, such as but not limited to a single board computer 352, alone or in combination with a field programmable gate array 356. The computer 352 or other processing components can be provided as part of the electronics 240. The processing and control components 316 generally operate to control the production of light having desired characteristics at desired times, determining the time of flight of light signals, and determining the amplitude of received light. The light processing and control components 316 can also include a memory or data storage 318 on which a leak detection and rate determination application 319 is stored. The application 319 can be executed by the computer 352 and/or the FPGA 356 to implement a cognitive neural network that operates to detect fugitive emissions leaks, and optionally to detect a rate of a detected leak, as described in detail elsewhere herein. Other functions performed by the processing and control components 316 can include correlating signals received from a target area 114 to a geographic location, determining a concentration of a gas of interest 122 within a target volume 106, storing data generated by the sensor system 104, transmitting data, receiving and implementing control commands, correlating three-dimensional sensor information with topographic maps, correlating three-dimensional sensor information with information from a two-dimensional context camera 244, or the like. In accordance with at least some embodiments, a dedicated steering mirror control section 360 can be provided. As can be appreciated by one of skill in the art after consideration of the present disclosure, the steering mirror control section 360 can include processors, memory, and drivers for controlling operation of the steering mirror 220, and in particular for controlling the volume of interest 106 encompassed by the field of view of the sensor system 104. The positioning, control, and power components section 320 can further include a global positioning system (GPS) receiver 364. In addition, an inertial measurement unit or inertial navigation unit 368 can be included. In accordance with further embodiments other components, such as power conditioning components 370, can be included in the positioning, control, and power components section 320.

The components associated with input/output functions 312 can include, as examples and without limitation, communications transmitters and receivers, positioning system receivers, and connections to power sources. More particularly, the components associated with the input/output functions 312 can include data links such as a ground datalink 372 and a radio frequency datalink 376 to support the real time transmission of data. As can be appreciated by one skill in the art after consideration of the present disclosure, data links 372 or 376 can output information obtained by the sensor system 104 to a remote or separate system or user. Other input/output components can include a GPS antenna 380, and connections to one or more power supplies 384.

Figure 4:
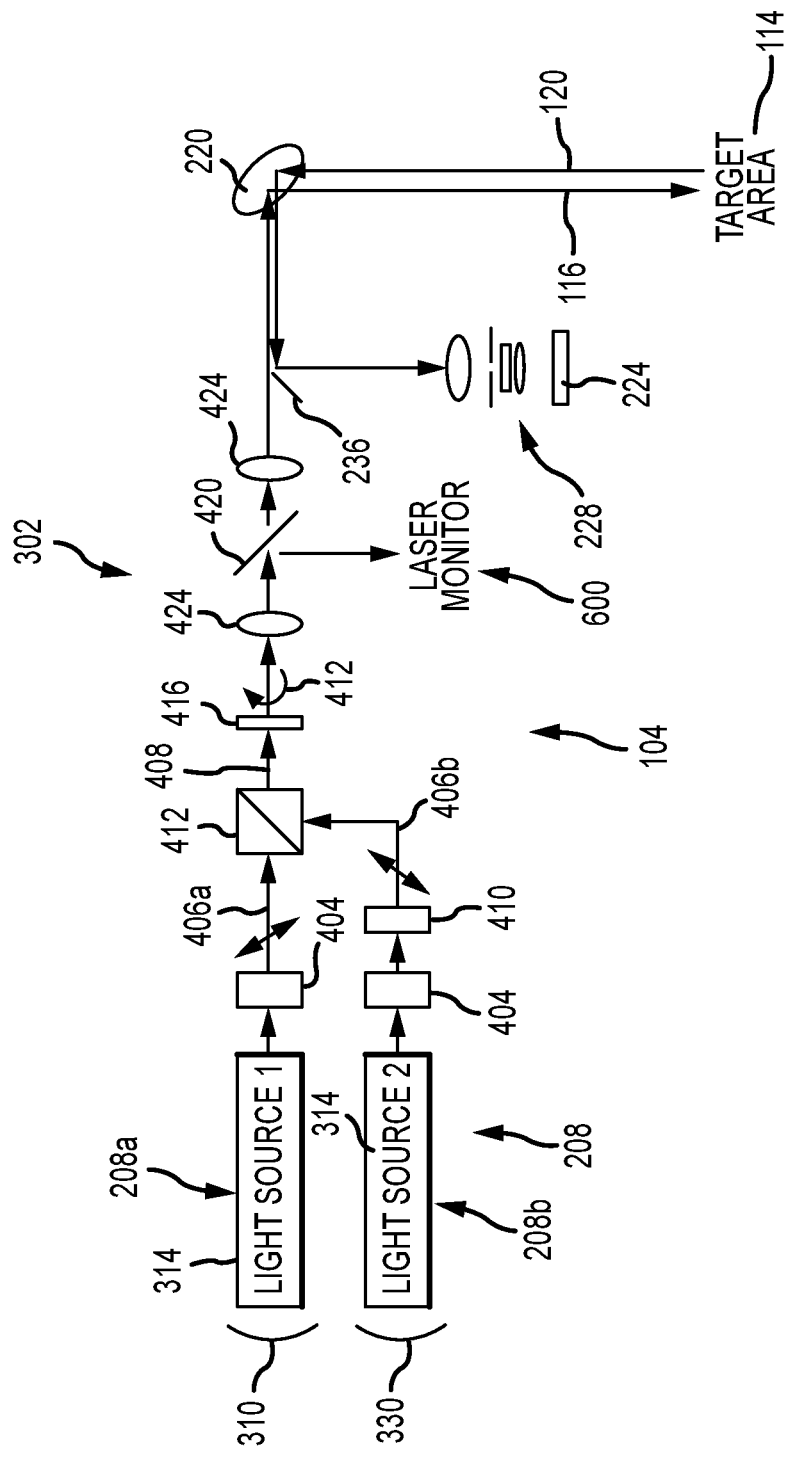
FIG. 4 is a schematic depiction of components of a sensor system in accordance with embodiments of the present disclosure.

FIG. 4 is a schematic depiction of components of a lidar or 3D sensor 302 included in a sensor system 104 in accordance with at least some embodiments of the present disclosure. In particular, this view of the sensor system 104 depicts components of the light source assemblies 208a and 208b, beam forming components, and detector components operable to obtain returns from particles, objects, and the like, and to detect the presence and measure the concentration of a gas of interest 122 within a target volume 106. In accordance with at least some embodiments of the present disclosure, and as shown in the figure, the sensor system 104 can include multiple light source assemblies 208. Each light source assembly 208 can include a light source 314, such as a laser. As an example, but without limitation, the light source 314 can include an Er:YAG laser. In addition, each light source assembly 208 can include a laser box or cavity 330. In accordance with embodiments of the present disclosure, the laser cavity 330 can include or be associated with a volume Bragg grating (VBG) 404 as an output coupler. As can be appreciated by one of skill in the art after consideration of the present disclosure, the VBG 404 of a light source 208 functions to select the wavelength that is output by the light source 208. Moreover, the operation of VBG 404 in this context is very reliable.

In accordance with embodiments of the present disclosure, the light 406a output by a first one of the light source assemblies 208a is selected to have a wavelength (a first wavelength) that is absorbed by a gas of interest 122, while the light output by a second one of the light source assemblies 208b is selected to have a wavelength (a second wavelength) that is not significantly absorbed by the gas of interest 122. Moreover, the first wavelength can be selected to be a wavelength other than the wavelength at which maximum absorption by the gas of interest 122 is observed, to increase the amount of light within the wavelength that is reflected back to the sensor system 104 when the gas of interest 122 is present within the target volume. The second wavelength can be selected to be a wavelength that experiences similar rates of absorption as the first wavelength by known or expected constituent gases within the ambient environment encompassing the target volume 106.

In accordance with still further embodiments of the present disclosure, the first light source assembly 208a is configured to output light 406a having a first linear polarization, while the second light source assembly 208b is configured to output light 406b having a second linear polarization that is orthogonal to the first polarization. The second light source assembly 208b can include or be associated with a ½ wave plate 410 to impose the second polarization on the output light 408b. The light 406 output by the light source assemblies 208 is placed along a common transmission path 408 by a polarization beam combiner 412. A quarter wave plate 416 is located along the common transmission path 408, and functions to transform the polarization of the light 406 from the light source assemblies 208 into circularly polarized light 412. As can be appreciated by one of skill in the art after consideration of the present disclosure, by transforming the polarization of the light 406 from the light sources 208 into a circular polarization, the interaction of light from both light sources 208 with surfaces within the target area 114 will be similar.

A pickoff mirror 420 is located along the path of the circularly polarized light 412. The pickoff mirror 420 directs a portion of the light to the laser monitor assembly 306. The portion of the light not redirected to the laser monitor assembly 306 by the pickoff mirror 420 passes through the beam splitter/combiner 236 to the steering mirror 220, which directs that light to the target area 114 as the transmitted beam 116. In accordance with embodiments of the present disclosure, an objective lens or lens assembly 424 can be provided between the quarter wave plate 416 and the pick off mirror 420, or between the pick off mirror 420 and the steering mirror 220.

The light 120 reflected from the target area 114 is received by the sensor system 104, and is directed by the steering mirror 220 to the mirror 236, and through the receive telescope 228, to the detector 224. The receive telescope 228 may be a reflecting telescope, including off-axis or Cassegrain primary reflectors and fold mirrors, a field-stop, focusing lenses and filters, as appropriate to manage the placement of light onto the detector 224. Alternatively, the receive telescope 228 may be a refracting set of objective lenses with stops and filters as appropriate. In accordance with embodiments of the present disclosure, the detector 224 may comprise a single pixel detector. In accordance with still other embodiments of the present disclosure, the detector 224 may comprise a multiple pixel detector, such as a two-dimensional array detector, for example where the sensor system 104 incorporates a flash LIDAR sensor. The detector 224 operates to detect a time of arrival and an amplitude of received light. Moreover, the detector 224 can be operated to detect returns, including light reflected by particles, or other materials or objects at a selected rage or set of ranges. As an example, a detector 224 may comprise a 10 bit single pixel detector. As another example, a detector 224 may comprise a 10 bit detector with a 128 by 128 array of pixels, or other two dimensional array of pixels (i.e. the detector 224 may comprise an imaging detector to implement a flash LIDAR system). The receive telescope 228 can operate to focus the received light 120 onto the detector 224.

Figure 5:
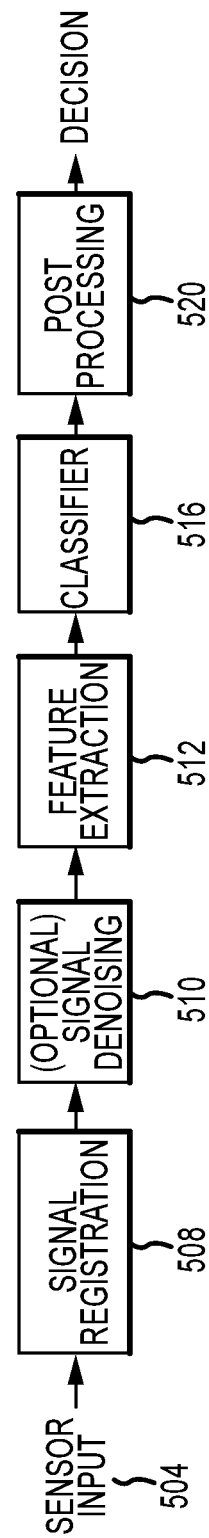
FIG. 5 is a flowchart depicting aspects of a method for detecting emissions in accordance with embodiments of the present disclosure.

FIG. 5 is a flowchart depicting aspects of a deep learning method or process that can be applied in connection with the detection of a gas of interest and further with the detection of a source and rate of emissions in accordance with embodiments of the present disclosure. As can be appreciated by one of skill in the art, deep learning methods can incorporate several layers of neural networks. Data representations are learned, with multiple levels of abstraction using a training set. Any type of neural network or machine learning process can be applied in connection with embodiments of the present disclosure. These can include deep neural networks, convolutional deep neural networks, deep Q networks, and recurrent neural networks. Initially, data collected by the sensor system 104 is provided as sensor input (step 504). Next, data from the system 302 included in the sensor system 104 is combined with location information, such as a from a GPS, INU, or other location determination or navigation system, and (optionally) context imagery from the context camera 244 that is also included in the sensor system 104 in a step of signal registration (step 508). At step 510, algorithms can optionally be applied to pre-condition and denoise signals. These can include straightforward approaches such as Gaussian smoothing. For lidar systems, the 3D terrain data can be combined with 2D data to find and remove sources of noise related to, for instance, structures and vegetation. They can also include neural networks as discussed herein in advanced approaches that characterize noise patterns generated by a particular instrument. At step 512, the system 302 data and the context camera 244 imagery is processed by a neural network, which extracts (identifies) features from the data. The neural network also operates to classify the features (step 516). In a step of post processing with lidar systems, the 2D and 3D data can be fused (step 520). Alternatively, both 2D and 3D data can be taken concurrently or in parallel, and the combined results can be fed into a further neural network step or layer. A decision, for example identifying a location of a detected emission plume, is then provided as an output (step 524). In general, embodiments of the present disclosure can perform the method using or in association with the execution of instructions, such as instructions encoded in an application 319, by the processing and control components 316. Alternatively or in addition, at least some steps of the method can be performed by processing facilities provided separately from the sensor system 104.

Figure 6:
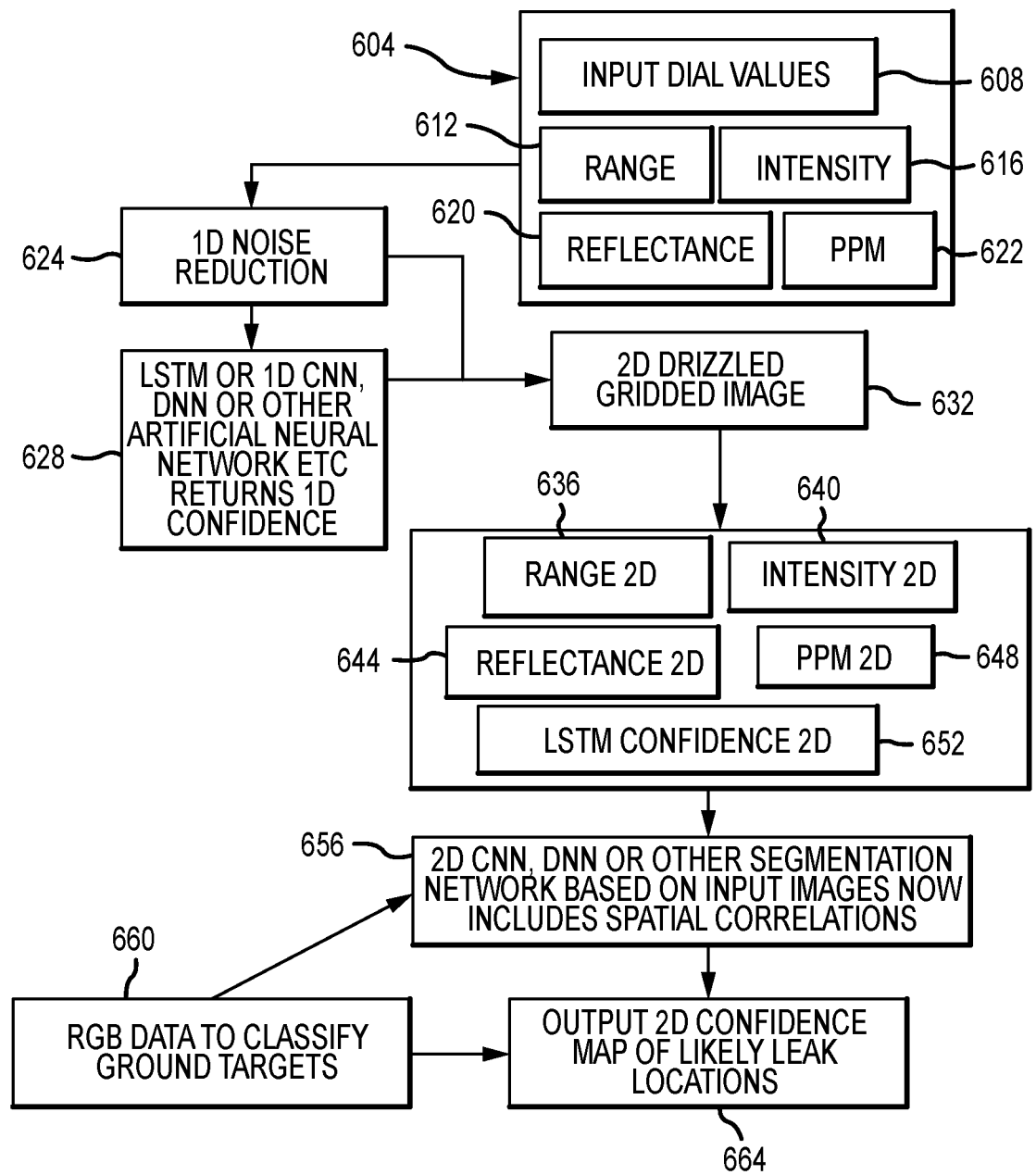
FIG. 6 depicts aspects of a process for detecting emissions in accordance with embodiments of the present disclosure.

Additional aspects of a process for detecting emissions in accordance with embodiments of the present disclosure are depicted in FIG. 6. In an initial data acquisition process (step 604), the sensor system 104 is operated to obtain measured values or data from a target volume 106 within an imaged area or scene 112 (608). In accordance with the least some embodiments of the present disclosure, the initial data acquisition process utilizes DIAL values obtained from a DIAL sensor system 104. In accordance with further embodiments, the initial data acquisition process utilizes an instrument other than a DIAL sensor system to obtain measured data from a target volume 106. For example, the measured data can include laser spectroscopy information, thermal imaging information, or other data. The measured data can include but is not limited to image data. Moreover, the measured data can be in the form of one dimensional (1D) lidar system 302 data. From the measured data values, the system 104 can determine various measured parameters. For example, in the case of a DIAL type sensor system 104, range 612, intensity 616, reflectance 620, and concentration (e.g. in parts per million (PPM) of a target gas 122) 622 can be determined using data collected from the scene by the sensor system 104. As can be appreciated by one of skill in the art after consideration of the present disclosure, the DIAL values of range 612, intensity 616, and reflectivity 620 are obtained from the return signal 120 of illumination light 116, typically of the wavelength that is not strongly absorbed by the gas of interest 122, while the concentration data 622 is obtained from a comparison of a strength of a return signal 120 of illumination light 116 of the first wavelength to a strength of a return signal of illumination light 116 of the second wavelength. Other lidar sensor systems 104 can provide range and intensity information. Moreover, the sensor system 104 can combine different instruments, for instance lidar systems, thermal or other cameras, and navigation systems, to provide measured data for processing.

At step 624, a 1D noise reduction process can be performed on the measured data. The noise reduction process can implement an adaptive filtering process, and can include smoothing collected data. This smoothing can comprise averaging the collected intensity, PPM or other data within a moving window. As an example, the moving window can include data collected over the past and relative future for 5-10 seconds. In accordance with further embodiments, the 1D noise reduction process can include Fourier processing to remove background noise. The filtering or Fourier processing can include filtering signals that are collected outside of periods during which lidar returns are expected.

At step 628, the noise reduced input values are processed by a neural network, also referred to herein as a first neural network, that has been trained to recognize data indicative of an emission plume. The first neural network can provide a 1D confidence value regarding the likelihood that an emission source or leak of a gas of interest 122 is present within a scene 112. Note that one of the inherent advantages of a neural network approach is the ability to perform analysis in the presence of noise, and thus the filtering step is an optional intermediate step. The raw measured values or noise reduced values can be provided to the first neural network as time series data or spatial and temporal correlation data. This data can include the detection of PPM data 622 indicating that a target gas 122 is present within a target volume 106 at concentrations higher than would be expected in the absence of a leak. The neural network can include, for example, a recurrent neural network, such as a long short term memory (LSTM), a 1D convolutional neural network (CNN), a deep neural network (DNN), or any other neural network.

The 1D confidence value for some or all of the input values determined at step 628, and the noise reduced data produced in the step of 1D noise reduction 624, is used to form 2D image data by gridding the 1D confidence data (step 632). As an example, a 2D image can be formed using the drizzle method. As can be appreciated by one of skill in the art after consideration of the present disclosure, the drizzle method can be used whether the lidar system 302 incorporates a single or multiple pixel detector 224. The 2D image data can include or be correlated with one or more of range 636, intensity 640, reflectance 644, gas (i.e. gas of interest 122) concentration 648, and confidence data 652, gridded across the 2D area from which the input values were collected. If 2D confidence data 652 is included in the 2D image data, it can be obtained using a long short-term memory unit or process of a neural network.

The 2D data, including the 1D confidence data, is then processed by a neural network, also referred to herein as a second neural network, to provide a 2D confidence value that an emission of a gas of interest is present within the scene 112 (step 656). The neural network processing performed at this step includes spatial correlations. For instance, the range 636, intensity 640, reflectance 644, concentration 648, and determined confidence 652 can all be spatially correlated. The neural network used to process the 2D data can include a CNN, DNN, or other segmentation network. As an example, the second neural network is generally trained to recognize cloud like returns associated with PPM data of a certain level as indicating an emission plume, and to discount the likelihood that returns determined to be associated with hard edges, such as building edges, are themselves indicative of an emission plume.

At step 660, red-green-blue (RGB) image data, or visual imagery obtained from the target area or scene encompassing the target volume 106 using a context camera 244 is combined with the spatially correlated measured values initially. For example, location data from a GPS receiver, IMU 368, or both can be used to match image data from the context camera 244 with the spatially correlated measured values. The combination of the RGB data and the processed 2D data is then provided as an output in the form of a map of likely emission locations (step 664). As an alternative or in addition to a 2D map of emission locations, a listing of locations, for instance by latitude and longitude or some other coordinate system, can be output. Moreover, the output can include confidence values regarding the likelihood of a leak at different locations within the map. The output can be presented by a user output device that is local to the sensor system 104, or it can be transmitted to another system or node, for example via an RF real-time link or other connectivity.

As can be appreciated by one of skill in the art after consideration of the present disclosure, the RGB data obtained by the context camera 244 may comprise visual imagery that assists a user in locating a leak in the physical environment. Alternatively or in addition, the RGB data can be input to the CNN implemented by the application 319, and image recognition processing can be applied to identify objects, structures, topographical features, or other characteristics of the scene captured within the image by the context camera 244. Any such characteristics can then be correlated with the 2D image information obtained using the lidar system 302, which can in turn assist in providing an enhanced 2D confidence value.

Figure 7:
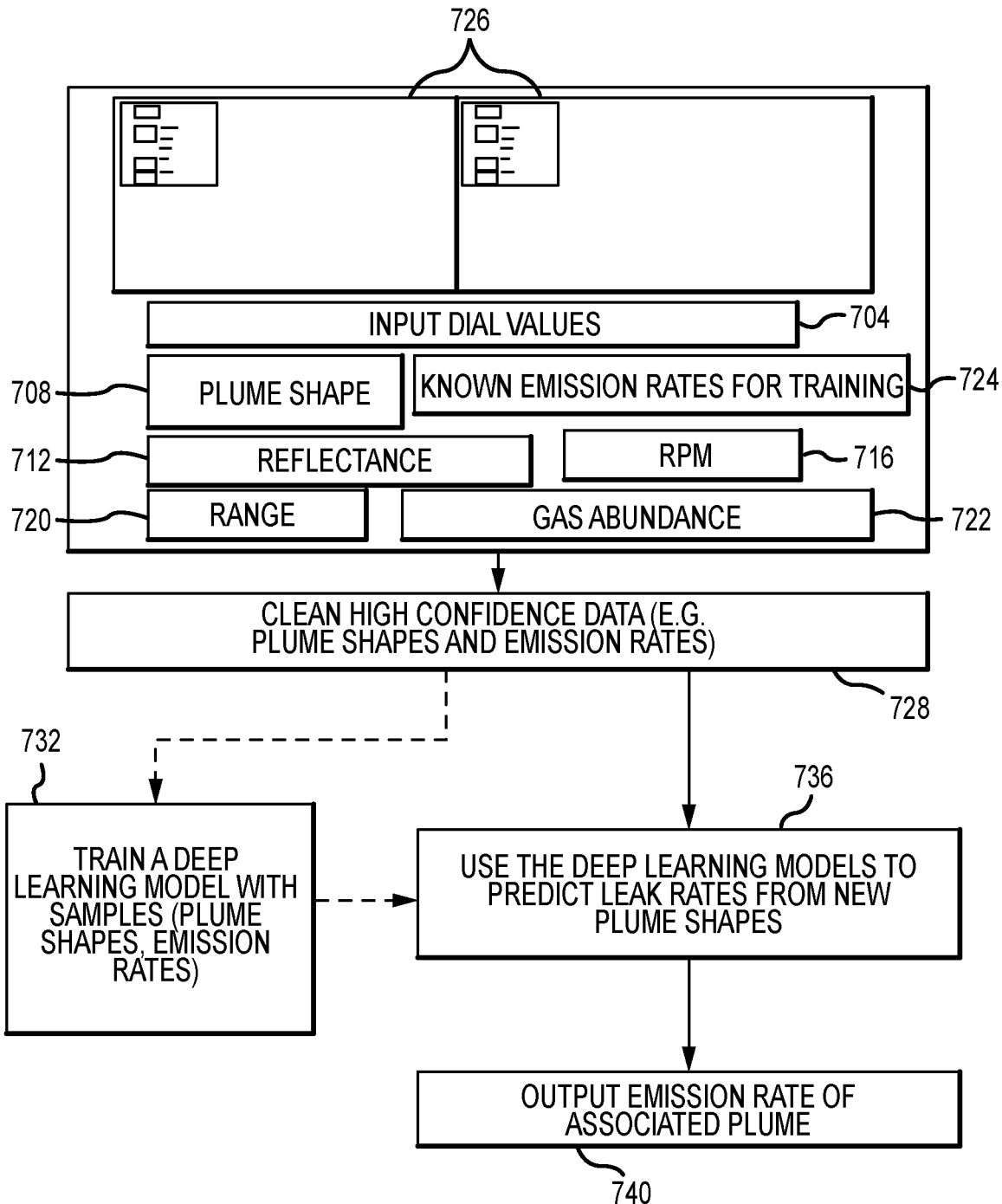
FIG. 7 depicts aspects of a process for detecting a rate of emissions in accordance with embodiments of the present disclosure.

FIG. 7 depicts aspects of a process for detecting a rate of emissions in accordance with embodiments of the present disclosure. Initially, at step 704, the map of emissions obtained at step 664 of the process for detecting emissions is provided as an input. This input data can be provided to a processing system, such as the processing section 308 of the sensor system 104, and/or another processing system or device in communication with or receiving data from the sensor system 104. This data can include the shape of a detected plume 708, reflectance data 712, concentration or PPM data 716, range data 720, and gas abundance data 722. In accordance with at least some embodiments of the present disclosure, the input data regarding the shape 708, the concentration 716, and/or the abundance 722 of the detected plume can include or be associated with 3D data. Moreover, the range data 720 obtained by the sensor system 104 can include information regarding the topography or morphology 726 of the area around or in the vicinity of a detected emission plume that is detected as the data regarding the shape and concentration of that plume is obtained. Alternatively or in addition, information regarding the topography or morphology 726 of the area around or in the vicinity of a detected plume can be obtained through a separate instrument or source, including but not limited to previously conducted mapping or survey operations. Such topographical information 726 can be in the form of 3D data.

Because the data provided at step 704 has been cleaned and validated using the process described above in connection with FIG. 6, it is particularly well suited for further processing by an additional neural network. Accordingly, at step 728 the cleaned and validated data is provided to a neural network, also refereed to herein as a third neural network, implemented by the processing section 308 and/or a related system. Moreover, the third neural network can be implemented by an application 319 stored in memory 318 and executed by a computer 314, FPGA 356, or other processing resource or set of resources included in the sensor system 104.

During a training step (step 732), known emission rate data 724 and data concerning the related plumes, such as plume shapes, intensity, reflectance, range, background topography or morphology 726, concentration data, and ancillary imagery, such as RGB images of the area, or the like, is input to the neural network implemented by the application 319. The data concerning the related plumes can include data in the form of DIAL measurement data taken from the emission associated with the known emission rate data 724.

The trained third neural network can then be used to predict or determine leak rates from the plume shapes associated with new emissions represented by the cleaned and validated data from the emissions detection processes described previously (step 736). Moreover, embodiments of the present disclosure can utilize the measured values obtained by the sensor system, such as the DIAL data obtained by a sensor system 104 incorporating a DIAL type lidar system 302, regarding characteristics of a gas of interest 122 within a scene 112, alone or in combination with topographical information 726 concerning the scene 112. This enables the provision of enhanced estimates of a leak rate, by accounting for the presence of valleys, hills, or other features that might influence the characteristics of a detected plume of gas 122. An estimated or determined emission rate for the plume associated with the detected emission (i.e. gas 122) can then be provided as an output (step 740). For example, a 2D or 3D map of a scene 112 can be used to present image data from a context camera, with an overlay of location and estimated emission rate information for a gas or gases or interest. Moreover, topographical information 726 can be included in the output. As a particular example, different emission rates for different areas within a scene can be indicated visually by different overlay densities or colors. As an alternative or in addition to a map of emission locations and emission rates, a listing of locations, for instance by latitude and longitude or some other coordinate system, can be output, together with an indication of a determined or predicted emission rate. The output can be presented by a user output device that is local to the sensor system 104, or it can be transmitted to another system or node, for example via an RF real-time link or other connectivity.

Embodiments of the present disclosure provide a sensor system 104 that can be carried by a platform 108, such as but not limited to a mobile platform, that is capable of remotely detecting emissions of a gas of interest 122 into the atmosphere. Detection sensitivity and accuracy can be enhanced over conventional techniques, by the use of noise reduction techniques as described herein. Alternatively or in addition, embodiments of the present disclosure can enable improved sensitivity and accuracy in detecting emissions of gas 122 into the environment by processing data obtained using a lidar sensor 302 using a CNN, DNN, or other segmentation network implemented by an application that can be stored on and executed by the processing resources of a sensor system 104 carried by an aircraft that integrates the processing resources with a lidar sensor 302. Moreover, a sensor system 104 in accordance with embodiments of the present disclosure can perform gas detection in real-time or near real-time, where near real-time is after a delay of 1 second or less.

In accordance with further embodiments of the present disclosure, emission rates for a detected source can be determined by the sensor system 104. Moreover, topographical data can be correlated and used in combination with the detection information to provide accurate location information regarding emissions and determinations of emission rates. In addition, information regarding objects within a scene 112, can be utilized in assigning or determining a confidence value regarding a detected source, or a rate of a detected source. Moreover, emission rates can be estimated using a sensor system 104 as described herein without requiring information regarding meteorological conditions, such as wind speeds at the site of the emission. Embodiments of the present disclosure can be implemented through a system operating autonomously, and thus without requiring manual estimations made from visual observations. Moreover, emissions rates can be determined using active and passive measurement systems, and furthermore can be determined in real-time or near real-time.

The foregoing description has been presented for purposes of illustration and description. Further, the description is not intended to limit the disclosed systems and methods to the forms disclosed herein. Consequently, variations and modifications commensurate with the above teachings, within the skill or knowledge of the relevant art, are within the scope of the present disclosure. The embodiments described hereinabove are further intended to explain the best mode presently known of practicing the disclosed systems and methods, and to enable others skilled in the art to utilize the disclosed systems and methods in such or in other embodiments and with various modifications required by the particular application or use. It is intended that the appended claims be construed to include alternative embodiments to the extent permitted by the prior art.

What is claimed is:

1. A method for detecting gas plumes, comprising:
obtaining data for a plurality of points within a scene, wherein the data includes a concentration value for a gas of interest at each of a plurality of different locations within a scene;
processing the data including the concentration value for the gas of interest at each of the plurality of different locations within the scene in a neural network to obtain a confidence value;
gridding the obtained and processed data to obtain 2D data;
processing the 2D data in a neural network to obtain a 2D confidence value;
spatially correlating the 2D data; and
outputting the spatially correlated 2D data as a map of likely emission locations for the gas of interest.

2. The method of claim 1, removing noise from the data prior to processing the data.

3. The method of claim 1, wherein the 2D data is associated with concentration data concerning a gas of interest.

4. The method of claim 1, wherein the 2D data is associated with range data.

5. The method of claim 4, wherein the 2D data is associated with reflectance data.

6. The method of claim 5, wherein the 2D data is processed using a long short-term memory process.

7. The method of claim 6, wherein the 2D data is processed by a neural network to provide the 2D confidence value.

8. The method of claim 7, wherein the 2D data is spatially correlated.

9. The method of claim 8, further comprising:
determining from the processing of the data by the neural network that an emission of a gas of interest is present.

10. The method of claim 1, wherein the map of likely emission locations is overlayed on an image of the scene.

11. The method of claim 10, wherein the data including the concentration value for the gas of interest at each of the plurality of different locations with the scene is obtained by a first sensor carried by a first platform, and wherein the image of the scene on which the map of likely emission locations is overlayed is obtained by a context camera carried by the first platform.

12. The method of claim 11, wherein the first sensor includes a light detection and ranging system.

13. The method of claim 1, wherein outputting a map of likely emission locations includes outputting a depiction of a shape of a plume of the gas of interest.

14. The method of claim 1, further comprising:
outputting a rate of an emission of the gas of interest.

15. A method for detecting gas plumes, comprising:
obtaining data for a plurality of points within a scene;
processing the data in a neural network to obtain a confidence value;
gridding 1D data sources to obtain 2D data,
processing the 2D data in a neural network to obtain a 2D confidence value, wherein the 2D data is associated with concentration data concerning a gas of interest, wherein 2D data is associated with range data, wherein the 2D data is associated with reflectance data, wherein the 2D data is processed using a long short-term memory process, wherein the 2D data is processed by a neural network to provide the 2D confidence value, and wherein the 2D data is spatially correlated;
determining from the processing of the data by the neural network that an emission of the gas of interest is present;
determining a shape of a plume of the gas of interest; and
determining a rate of the emission of the gas of interest.

16. The method of claim 15, wherein the data includes a concentration value for a gas of interest.

17. The method of claim 16, further comprising:
fusing the 2D data with red, green, blue (RGB) image data; and
outputting a map indicating locations of likely emission sources.

18. The method of claim 15, further comprising:
training the neural network using samples of plume shapes and emission rates.

19. The method of claim 15, further comprising:
outputting a map depicting the shape of the plume of the gas of interest.

20. The method of claim 19, wherein the map depicting the shape of the plume of the gas of interest is overlayed on an image of the scene.

* * * * *